US006572817B1

(12) United States Patent
Fields et al.

(10) Patent No.: US 6,572,817 B1
(45) Date of Patent: Jun. 3, 2003

(54) OZONE ENHANCING SYSTEM

(75) Inventors: William M. Fields, Evergreen, CO (US); Donald L. Boyd, Arvada, CO (US)

(73) Assignee: Universal Water Technologies, LLC, Englewood, CO (US)

( * ) Notice: Subject to any disclaimer, the term of this patent is extended or adjusted under 35 U.S.C. 154(b) by 0 days.

(21) Appl. No.: 09/552,640

(22) Filed: Apr. 19, 2000

Related U.S. Application Data

(60) Provisional application No. 60/130,838, filed on Apr. 22, 1999.

(51) Int. Cl.[7] ............ A61L 2/00; B01D 15/00; B01D 39/00
(52) U.S. Cl. ............ 422/24; 422/32; 422/121; 422/186.07; 422/186.3; 422/300; 422/305; 210/192; 210/198.1; 210/748; 210/760; 96/224; 26/DIG. 42
(58) Field of Search ............ 422/1, 4, 22, 24, 422/28–30, 32, 121, 186.07–186.12, 186.21, 186.3, 186.7–188, 292, 305, 906–907; 210/748, 760, 192, 198.1; 96/224; 261/DIG. 42

(56) References Cited

U.S. PATENT DOCUMENTS

| 3,748,262 A | | 7/1973 | Lee et al. ............ 210/63 |
| 4,121,107 A | * | 10/1978 | Bachmann |
| 4,504,445 A | * | 3/1985 | Walz |
| 5,520,888 A | * | 5/1996 | Berndt |

FOREIGN PATENT DOCUMENTS

| JP | 410071195 | * | 3/1998 | ............ A61L/9/015 |

* cited by examiner

Primary Examiner—Robert J. Warden, Sr.
Assistant Examiner—Monzer R. Chorbaji
(74) Attorney, Agent, or Firm—Patton Boggs LLP

(57) ABSTRACT

A system for treating a contaminated liquid wherein atmospheric air is fed into an oxygen generator with the resulting gases fed into an ozone generator and the resulting gases fed into a treatment tower as the contaminated liquid flows through the treatment tower is modified by locating apparatus between the oxygen generator and the ozone generator which apparatus receives the gases from the oxygen generator, ionizes such gases and feeds the ionized gases to the ozone generator.

11 Claims, 1 Drawing Sheet

OZONE ENHANCING SYSTEM

This application claims the benefit of U.S. Provisional Application No. 60/130,838 filed Apr. 22, 1999, which is hereby incorporated by reference for all that is disclosed therein.

FIELD OF THE INVENTION

This invention relates generally to the treatment of liquids and more particularly to the treatment of liquids to remove deleterious or undesirable matter.

BACKGROUND OF THE INVENTION

There are many instances wherein it is necessary to treat a variety of liquids to remove deleterious or undesirable matter therefrom. In many parts of the world, there exists a need for treating water so that it can be used in a variety of different ways such as potable water, industrial uses, treating of effluent, bleaching of pulp in the pulp and paper industry and many other uses. In many locations there are a variety of sources available for providing water but the water from such sources is contaminated with deleterious or undesirable matter therein. In some instances, the contaminated water is treated with treated gases issuing from an ozone generator to remove such deleterious or undesirable matter. While several types of apparatus and methods have been used to treat such water with such treated gases, there still remains a need for an efficient and economical system for the treatment of such water with such treated gases. In one of the presently used systems to treat contaminated water with treated gases issuing from an ozone generator, the apparatus uses an oxygen generator wherein the atmospheric air is treated to separate the oxygen therefrom. The separated oxygen is then fed into an ozone generator that converts the oxygen into treated gases which are then passed through contaminated water flowing through a treatment tower, preferably using a diffuser to bubble the treated gases through the contaminated water. In a somewhat less efficient system, atmospheric air is fed directly into the ozone generator. In such a system, the contaminated water is introduced into the treatment tower and as it passes through the treatment tower, it is subjected to the treated gases and the treated water then exists the treatment tower. While the foregoing systems do provide a treatment for the contaminated water, it is desirable to increase the efficiency of and lower the economics of such systems.

BRIEF DESCRIPTION OF THE INVENTION

This invention provides apparatus and method for the treatment of contaminated liquids, which in the preferred embodiment of the invention is contaminated water, with treated gases issuing from an ozone generator so as to remove or at least substantially reduce the deleterious or undesirable matter therefrom.

In a preferred embodiment of the invention, atmospheric air is fed into an oxygen generator wherein the oxygen, $O_2$, is separated from the atmospheric air. The separated oxygen is fed into a housing containing at least one ultra violet lamp, but preferable a plurality of ultra violet lamps. In the preferred embodiments of the invention, the ultra violet lamps are chosen from those that emit light between about 185 and 254 nanometers. The type of ultra violet lamp chosen for use with this invention depends upon the contaminated water being treated. The ultra violet lamps treat the oxygen being fed into the housing so that oxygens $O_1$, $O_2$ and $O_3$ exit from the housing. The exiting oxygens $O_1$, $O_2$ and $O_3$ are fed into an ozone generator which treats the oxygens $O_1$, $O_2$ and $O_3$ and the treated gases exit from the ozone generator which treated gases contain an abundance of ionized ozone, $O_3$. A continuous flow of contaminated water is introduced into a treatment tower having a diffuser located therein. The treated gases from the ozone generator are fed into the diffuser to be bubbled through the contaminated water passing through the treatment tower so that uncontaminated water exits from the treatment tower. While a diffuser is used in the description of this invention, it is understood that the various conventional methods and apparatus used to treat a liquid with gases can be used instead of a diffuser. As described below, the treated gases exiting from the ozone generator in the preferred embodiments of this invention are of a nature that a substantially less quantity of the treated gases may be used to remove the contaminated matter in the same quantity of contaminated water as in existing systems.

BRIEF DESCRIPTIONS OF THE DRAWING

An illustrative and presently preferred embodiment of the invention is illustrated in the drawing in which.

DETAILED DESCRIPTION OF THE INVENTION

Figure 1:
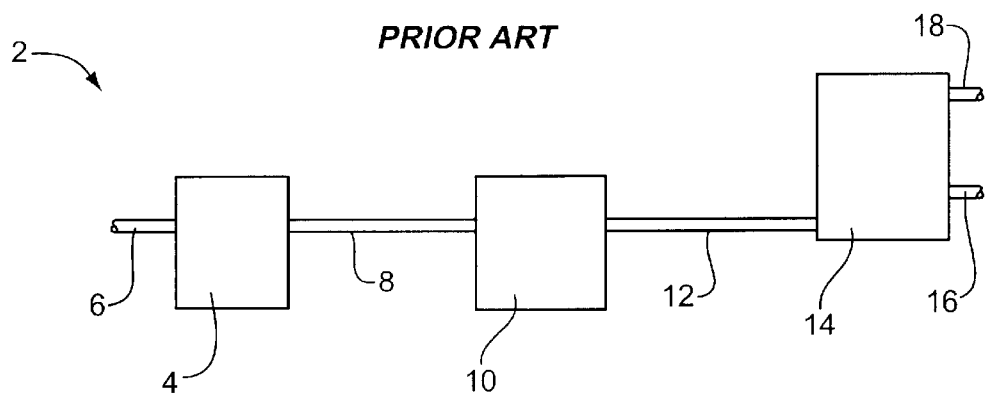
FIG. 1 is a schematic representation of a prior art system for the treatment of contaminated water with treated gases issuing from an ozone generator.

In FIG. 1, there is illustrated apparatus 2 for treating a continuous flow of contaminated water with treated gases issuing from an ozone generator. An oxygen generator 4 receives atmospheric air through inlet pipe 6 and emits treated gases, primarily oxygen, $O_2$, through outlet pipe 8. The treated gases in outlet pipe 8 are fed into an ozone generator 10. The treated gases, containing ozone, $O_3$, from the ozone generator pass through pipe 12 into a diffuser (not shown in the bottom of the treatment tower 14. Contaminated water is fed into the treatment tower 14 through inlet pipe 16 where it is treated with the treated gases from the ozone generator 10 to remove or substantially reduce the deleterious or undesirable matter from the contaminated water. The treated uncontaminated water leaves the treatment tower 14 through the outlet pipe 18. If desired, the oxygen generator 4 may not be used and atmospheric air is introduced directly into the ozone generator 10. However, such a system is not as efficient as the system illustrated in FIG. 1.

Figure 2:
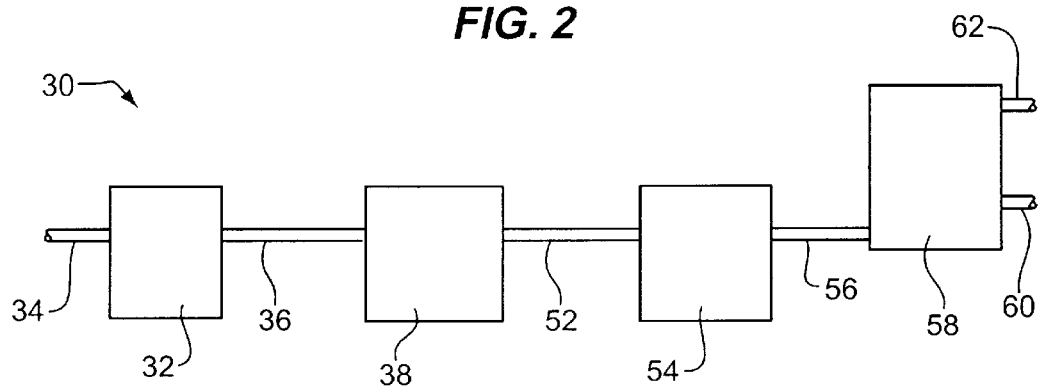
FIG. 2 is a schematic illustration of a preferred embodiment of the invention for the treatment of contaminated water with treated gases issuing from an ozone generator.

A preferred embodiment of apparatus 30 of this invention used for the treatment of contaminated water with treated gases issuing from an ozone generator is illustrated schematically in FIG. 2. Atmospheric air is fed into an oxygen generator 32, similar to oxygen generator 4, through inlet pipe 34. Treated gases, primarily oxygen, $O_2$, issue from the oxygen generator 32 through outlet pipe 36 and flow into a housing 38. At least one ultra violet lamp and preferably a plurality of ultra violet lamps are mounted in the housing 38. The ultra violet lamp is chosen to emit light in the frequency range of between about 185 and 254 nanometers depending on the characteristics of the contaminated water to be treated.

Figure 3:
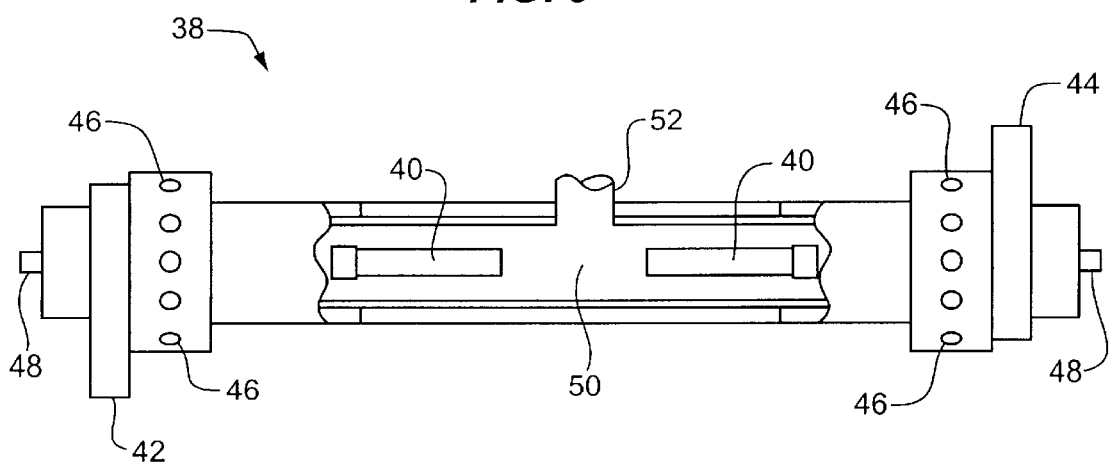
FIG. 3 is an illustration of an apparatus used in the preferred embodiment of the invention illustrated in FIG. 2.

In FIG. 3, there is illustrated one type of housing 38 in which one ultra violet lamp 40 is mounted. The housing 38 is manufactured by Fields & Boyd Inc. under the trade designation ION GAS GENERATOR. Other types of housings are also provided in which a plurality of ultra violet lamps are mounted. The housing 38, FIG. 3, has two spaced apart mounting devices 42 and 44. A plurality of openings 46 are located at each end of the housing 38 so that the gases to be subjected to the ultra violet lamp or lamps 40 may be passed into the housing 38. Mounting means 48 are provided at each end of the housing 38 for mounting the ultra violet lamp 40. The gases to be treated enter through the openings 46 and move through filters and various passageways into the hollow body 50 to be subjected to treatment by the ultra violet lamp or lamps 40. The treated gases in the hollow body 50 exit the housing 38 through outlet pipe 52 and enter into an ozone generator 54, similar to the ozone generator 10. The treated gases issuing from the housing 38 are ionized oxygens $O_1$, $O_2$ and $O_3$ and preferably have concentrated oxygen. The treated gases preferably containing an abundance of ionized ozone, $O_3$, pass from the ozone generator 54 through pipe 56 into a diffuser (not shown) in the bottom of the treatment tower 58. As stated above, the ionized ozone can be introduced using other types of conventional methods and apparatus used to treat a liquid with gases. Contaminated water is fed into the treatment tower 58 through inlet pipe 60 where it is treated with the treated gases from the ozone generator 54 to remove or substantially reduce the deleterious or undesirable matter from the contaminated water. The treated uncontaminated water leaves the treatment tower 58 through the outlet pipe 62.

A series of tests were conducted to determine the relative efficiencies of the apparatus 2 illustrated in FIG. 1 and the apparatus 30 illustrated in FIG. 2. Instead of passing contaminated water through the treatment towers 14 and 58, the same amount of the same contaminated water was placed in each treatment tower 14 and 58. The same quantity of treated gases was passed from the ozone generators 10 and 54 into each of the treatment towers 14 and 58. The diffusers in the treatment towers 14 and 58 were the same. The treated gases passing through the contaminated water were collected and measured. The treated gases passing through the contaminated water in the treatment tower 14 were absorbed in the amounts between about 0.1 to 0.5 mg per liter while the treated gases passing through the contaminated water in the treatment tower 58 were absorbed in the amount between about 1.4 to 3.0 mg per liter. In these tests, two ultra violet lamps 40 were mounted in the housing 38 and each lamp emitted light at a frequency of 185 nanometers. Therefore, the quantity of treated gases issuing from the ozone generator 10 in FIG. 1 needed to treat a flow of contaminated water through the treatment tower 14 is three times greater than the quantity of treated gases issuing from the ozone generator 54 in FIG. 2 needed to treat the same flow of contaminated water through the treatment tower 58.

The treated water issuing from the outlet pipe can be used for a variety of purposes such as potable water, treatment of effluent, water for use in the pulp and paper industry for the bleaching of fiber and in other instances such as wherein chlorine is used to treat water.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A system for the production of enhanced ozone from atmospheric air, comprising:
    oxygen generator means, having an input port and an output port, for receiving atmospheric air through said input port, and outputting oxygen that is generated therein from said atmospheric air via said output port;
    oxygen ionizer means, connected to said oxygen generator means output port and connected to said oxygen, for generating ionized oxygen constituting at least two of $O_1$, $O_2$ and $O_3$; and
    ozone generator means, connected to said ionized means for producing a flow of ozone, generated from said ionized oxygen.

2. The system recited in claim 1 wherein said oxygen ionizer means comprises:
    a closed hollow housing; and
    at least one ultra violet lamp, emitting light in the frequency range of between about 185 and 254 nanometers, mounted in said closed hollow housing.

3. The system recited in claim 2 wherein said closed hollow housing comprises:
    a central body portion and opposite end portions;
    an inlet port located in at least one of said opposite end portions; and
    an outlet port located in said central body portion.

4. The system recited in claim 3 wherein said at least one ultra violet lamp is mounted between said at least one of said opposite end portions and said outlet port.

5. A system for the production of enhanced ozone from atmospheric air, comprising:
    oxygen generator means, having an Input port and an output port, for receiving atmospheric air through said input port, and outputting oxygen that is generated therein from said atmospheric air via said output port;
    oxygen ionizer means, responsive to said oxygen received from said output port of said oxygen generator means, for generating ionized oxygen constituting at least two of $O_1$, $O_2$ and $O_3$, comprising:
        a housing forming a fluid flow path,
        an input port located at a first end of said fluid flow path,
        an output port located at a second end of said fluid flow port,
        an ultraviolet lamp emitting light in the frequency range of between about 185 and 254 nanometers mounted in said fluid flow path; and
    ozone generator means, responsive to receipt of said ionized oxygen, for producing a flow of ozone, generated from said ionized oxygen.

6. A system for the production of enhanced ozone from atmospheric air, comprising:
    Oxygen generator means, having an input port and an output port, for receiving atmospheric air through said input port, and outputting oxygen that is generated therein from said atmospheric air via said output port;
    Oxygen ionizer means, connected to said output port of said oxygen generator means, for generating ionized oxygen constituting at least two of $O_1$, $O_2$ and $O_3$, comprising:
        A housing forming a fluid flow path,
        An input port located at a first end of said fluid flow path said input port of said oxygen ionizer means being connected to said output port of said oxygen generator means, An output port located at a second end of said fluid flow path, An ultraviolet lamp, emitting light in the frequency range of between about 185 and 254 nanometers, mounted in said fluid flow path; and ozone generator means, connected to said output port of said oxygen ionizer means for producing a flow of ozone, generated from said ionized oxygen.

7. The system of claim 6 further comprising:

Treatment tower means, connected to said ozone generator means for inserting said flow of ozone into a stream of contaminated fluid flowing through said treatment tower means.

8. The system of claim 1 further comprising:

Treatment tower means, connected to said ozone generator means for inserting said flow of ozone into a stream of contaminated fluid flowing through said treatment tower means.

9. The method of claim 8 wherein said step of generating ionized oxygen comprises:

generating light in the frequency range of between about 185 and 254 nanometers.

10. The method of claim 9 wherein said step of generating ionized oxygen further comprises:

exposing said oxygen to said light generated in the frequency range of between about 185 and 254 nanometers.

11. The method of claim 10 wherein said step of exposing oxygen further comprises:

passing a flow of said oxygen from said output port of said oxygen generator through said light generated in the frequency range of between about 185 and 254 nanometers.

\* \* \* \* \*